United States Patent [19]
Craig et al.

[11] Patent Number: 6,089,617
[45] Date of Patent: Jul. 18, 2000

[54] SYSTEM FOR ATTACHING A TUBULAR DEVICE TO A PLANAR DEVICE

[75] Inventors: Stephen R. Craig, Wilmington, Del.; James A. Bristow, Elkton, Md.

[73] Assignee: Hewlett-Packard Company, Palo Alto, Calif.

[21] Appl. No.: 09/124,521

[22] Filed: Jul. 29, 1998

Related U.S. Application Data

[63] Continuation-in-part of application No. 08/903,843, Jul. 31, 1997, Pat. No. 5,988,703.

[51] Int. Cl.$^7$ ........................................................ F16L 13/02
[52] U.S. Cl. ...................................... 285/288.1; 285/136.1; 285/124.1; 219/93; 228/164
[58] Field of Search ................................ 285/21.1, 136.1, 285/288.1, 124.1; 219/93, 505; 228/164; 29/890.148

[56] References Cited

U.S. PATENT DOCUMENTS

| | | |
|---|---|---|
| 2,202,405 | 5/1940 | Smith . |
| 2,257,427 | 9/1941 | Parker . |
| 2,360,660 | 10/1944 | Eaton et al. . |
| 2,903,562 | 9/1959 | Emmons et al. . |
| 4,480,166 | 10/1984 | Leech . |
| 4,677,271 | 6/1987 | Opprecht . |
| 4,901,135 | 2/1990 | Costigan . |
| 5,039,844 | 8/1991 | Nagahori . |
| 5,567,868 | 10/1996 | Craig et al. . |

*Primary Examiner*—Dave W. Arola

[57] ABSTRACT

A fluid connector system for connecting a tubular device such as a conduit having a fluid-bearing capability to a channel port having a fluid-bearing capability in a planar surface, thereby providing a substantially leak-free fluid communication between the conduit and the channel port. The conduit bore communicates with a conduit outlet located in a surface region on the outlet end of the conduit. Located within the outlet end surface region is a weld projection. The channel port is located in a receiver portion of a planar surface and communicates with a channel . A port surface region on the exterior of the planar surface encompasses the channel port. The outlet end surface region and the port surface region are complementary in that they may be superimposed so as to co-locate the conduit outlet and the channel port. The leading edge of the conduit outlet is oriented to contact the port surface region so as to define a line of contact. The weld projection and the material that underlies the line of contact are both formed of electrically resistive material suited to melting and subsequent fusion via resistive heating due to a brief application of an electric current. Accordingly, upon application of a current pulse that is sufficient to cause resistive heating at the weld projection, the weld projection and the material that underlies the line of contact are heated and fused. Upon cooling, the outlet end and the port surface region joined such that a hermetic seal is imposed about the juncture of the superimposed conduit outlet and channel port. A preferred embodiment of the fluid connector system is effective for connecting a conduit to a planar surface in a planar manifold assembly.

10 Claims, 6 Drawing Sheets

SYSTEM FOR ATTACHING A TUBULAR DEVICE TO A PLANAR DEVICE

CROSS REFERENCE TO RELATED APPLICATION

This application is a continuation in part of Application No. 08/903843, filed on Jul. 31, 1997 and now U.S. Pat. No. 5,988,703 in the name of Stephen R. Craig, the disclosure of which is included herein by reference.

FIELD OF THE INVENTION

The present invention relates to methods and apparatus for effecting fluid-tight connection of a tubular device to a planar surface in a planar device, and more particularly with a fluid connector system for use in connecting apparatus such as tubing to a port in planar manifold assembly operable in an analytical instrument.

BACKGROUND OF THE INVENTION

Instruments which rely upon regulated fluid flow are commonly employed in a wide variety of applications, such as sample purification, chemical analysis, clinical assay, and industrial processing. For many instruments, an extensive and complex array of tubular devices in the form of tubing, fittings, connectors, and the like are employed to provide the many flow paths that are necessary for optimum operation, and to effect the attachment of other devices such as sensors, valves, and the like.

Very often, such instruments devices require a complex arrangement of devices in a flow system having multiple flow paths. Generally, efficient operation of a flow system requires a combination of flow-through components, such as valves, sensors, columns, and connective tubing, with terminal components, such as needles, pumps, and drains. Different flow paths are frequently required to, for example, isolate a component from the flow system, include a component into the flow system, or rearrange the order of the components in the flow system. Further, there is the need to sense certain characteristics of the fluid flow at differing points in the flow paths. Examples of such sensed characteristics include the pressure, flow rate, and temperature of the fluid. Other characteristics related to the particular fluid flow include the presence or absence of a fluid component, such as an analyte or contaminant. Such needs are typically addressed by the use of fluid connectors for attachment of differing devices. Combinations of fluid connectors are sometimes necessary to provide flow paths among the flow-through components and terminal components employed in a flow system.

There exists the practical problem, therefore, of connecting an array of tubular devices that are required for the multitude of flow path combinations in a modern instrument. Another practical problem remains in connecting quite a large number of devices in a multitude of flow path combinations in a confined spaced within an instrument. The complexity of such systems also introduces reliability concerns. Because the instruments having these flow systems are sometimes mass-produced for automated or unattended operation, the cost and reliability of the fluid connection are features critical to successful operation of the instrument.

Another problem involves the proper orientation of all of the tubing, valves, sensors, and the like so as to allow the designer to achieve the desired combinations of flow paths, yet also provide an assembly that is compact, easily-manufactured, inexpensive, and reliable. The provision of fluid-tight connections in a complex fluid-handling assembly has become exceedingly problematic as the assembly is reduced in size.

In response to these problems, U.S. Pat. No. 5,567,868, issued to Craig et al., disclosed an instrument, preferably in the form of a chromatograph, that includes a computer, a pneumatic controller responsive to the computer, and planar manifold assembly. The planar manifold assembly includes one or more fluid-handling functional devices attached to a planar manifold. Multiple fluid-handling functional devices may then be coordinated and assembled so as to connect to pneumatic channels that are integrated in the planar manifold, and thus many of the fluid flow paths are integral to the planar manifold, which is itself quite compact and amenable to construction in a variety of shapes and configurations. The advantages of the planar manifold assembly include the reduction of external connections between fluid-handling functional devices (such as fittings, valves, sensors, and the like) by use of a single planar manifold for the provision of a plurality of flow paths. The fluid-handling functional devices that connect to the planar manifold are constructed to be surface-mounted to offer reliable, fluid-tight connection without the complexity and difficulty of previously-known pneumatic connections.

Nonetheless, there still remains a difficulty in effecting such simple, reliable, and inexpensive fluid connections between a tubular device and a port situated in a planar surface on a planar device. Such planar surfaces may be found on a machined part designed for use with the planar manifold assembly, such as a microminiature valve, or, in particular, on the above-described planar manifold. Conventional fluid connectors have several significant disadvantages that make them unsuitable for this task. Firstly, they require some type of fitting to be machined, brazed, or otherwise attached to the port, thus requiring a substantial fabrication cost and effort; secondly, they typically exhibit a dead space communicating with the ends of the fluid channels being coupled. A portion of the fluid emerging from the end of one channel quickly finds its way into the dead space but a relatively long time is required for it to enter the other channel. For example, in a tube connected by conventional compression fitting connector to a receiving fitting on a detector in a chromatograph, the concentration of a sample fluid emerging from one end of the tube must increase rapidly to a maximum value and then rapidly decay to zero to be detected as a chromatographic peak. When this high concentration enters the unswept dead space, it only leaves by diffusion which, as it is slow, causes the concentration peak to decay slowly . This undesirable phenomenon is known as tailing. As those skilled in the art are aware, such a phenomenon can make it difficult to detect separate components of the sample. Another significant disadvantage of conventional fluid connectors is that the fluid flowing through the fluid connector can be degraded by contact with large areas of less-than-inert surfaces of the device. Still another significant disadvantage of conventional fluid connectors is that planar fluid handling devices, such as the planar manifold assembly described hereinabove, are becoming even smaller and are designed to be assembled to form a compact, densely-populated arrangement of parts. Conventional fluid connectors, in contrast, remain undesirably large and bulky.

There is accordingly a need in many applications for a fluid connector system for use in effecting a fluid connection between a tubular device and a port on a planar surface in a planar device, wherein such a system would offer such attributes as: miniaturization, reliability, simplicity, robustness, ease in assembly and maintenance, and low cost.

SUMMARY OF THE INVENTION

The present invention provides a fluid connector system for connecting a tubular device, preferably provided in the form of a conduit having a fluid-bearing capability, to a port having a fluid-bearing capability located within a planar surface on a planar device, thereby providing a system for effecting a substantially leak-free fluid communication between the conduit and the tubular device.

A preferred method for coupling a tubular device to a channel port situated in the planar surface of planar device includes: a) providing the tubular device in the form of a conduit having an conduit outlet and a conduit outlet surface region that includes a weld projection; b) mounting the conduit outlet surface region onto a channel port surface region to engage the leading edge of the weld projection against the channel port surface region and to superimpose a conduit outlet and the channel port; c) urging the planar device and the conduit together to cause a line contact of the channel port surface region by the leading edge of the weld projection; and d) subjecting the conduit outlet surface region and the channel port surface region to a current flow therebetween sufficient to cause localized, intense heating at the leading edge of the weld projection and at the line of contact. Preferably, the weld projection is provided in an annular or similar closed geometric form when viewed along the central axis of the conduit, such that the desired configuration of the line contact will provide a complete seal about the conduit outlet and the channel port.

A first preferred embodiment of a fluid connector system may accordingly be constructed according to the present invention for coupling a tubular device to a channel port situated in the planar surface of planar device. The bore of the conduit communicates with a conduit outlet located at an outlet end of the conduit. Located at the outermost portion of the outlet end of the conduit, and encircling the conduit outlet, is a weld projection. Preferably, the outlet end of the conduit is flared such that an interior bore wall terminates at the weld projection. The channel is located in a receiving portion of a planar device and communicates with a channel port. A channel port surface region on the exterior of the planar assembly encompasses the channel port. The conduit outlet end and the channel port surface region are complementary in that they may be superimposed so as to co-locate the conduit outlet and the channel port. The leading edge of the weld projection is preferably shaped for circular line contact with the channel port surface region as the conduit outlet surface region is urged against the channel port surface region by a biasing force. The leading edge of the weld projection contacts the channel port surface region on the planar manifold in a fashion that defines a line of contact. The weld projection and the material that underlies the line of contact are both formed of electrically resistive material suited to melting and subsequent fusion via resistive heating due to a brief application of an electric current. Accordingly, upon application of a current pulse that flows between the weld projection and the channel port surface region, the current density of the pulse is concentrated at the line of contact and is sufficient to cause resistive heating of the weld projection and the material that underlies the line of contact. The weld projection and the material that underlies the line of contact are melted, thereby becoming fused together. Upon cooling, the channel port surface region and the outlet end of the conduit are found to be merged, and the weld projection and the line of contact are fused and thus no longer distinguishable, thus attaching the outlet end of the conduit to the channel port surface region such that a hermetic seal is imposed fabricated the juncture of the interior bore wall and channel port.

In a second preferred embodiment, the outlet end of the conduit need not be flared, and preferably forms a sharp, cylindrical peripheral edge. A first weld projection is located about the peripheral edge of the conduit outlet. The channel port is fabricated to include a second weld projection located at the uppermost peripheral edge of the channel port . This second weld projection is sized to receive an intermediary conical fitting that is placed between the first and second weld projections. That is, the interior side wall of the conical fitting is angled and sized so as to abut the sharp edge of the first weld projection. The exterior side wall of the conical fitting is similarly angled and sized so as to abut the sharp edge of the second weld projection. The conduit outlet surface region and the channel port surface regions are then superimposed so as to co-locate the conduit outlet, the conical fitting, and the channel port. The conical shape of the conical fitting causes the conical fitting to be self-aligned between the first and second weld projections to aid such co-location.

The leading edges of the first and second weld projections are respectively urged against the interior and exterior side walls of the conical fitting by a biasing force. The leading edge of each weld projection contacts the conical fitting in an opposing fashion that defines respective first and second circular lines of contact. Each weld projection and the material in the conical fitting that underlies each line of contact are formed of electrically resistive material suited to melting and subsequent fusion via resistive heating due to a brief application of an electric current. Accordingly, upon application of a current pulse that flows between the weld projections and the conical fitting, the current density of the pulse is concentrated at the first and second lines of contact and is sufficient to cause resistive heating of the first and second weld projections and of the material that underlies the lines of contact. The weld projections and the material that underlies the lines of contact are melted, thereby becoming fused together. Upon cooling, the first and second weld projections are fused to the conical fitting and thus are generally indistinguishable, thus rigidly joining the outlet end of the conduit, the conical fitting, and the channel port surface region such that a hermetic seal is imposed at the interfaces of the outlet end of the conduit, the conical fitting, and the channel port surface region. The conical fitting includes a central aperture so as to allow unimpeded fluid communication between the conduit bore and the channel port.

In a third preferred embodiment, the outlet end of the conduit need not be flared, and preferably forms a sharp, cylindrical peripheral edge. A first weld projection is located about the peripheral edge of the conduit outlet. The bore of the conduit communicates with a conduit outlet located at the outlet end of the conduit. The channel is located in a receiving portion of a planar device and communicates with a channel port. A channel port surface region on the exterior of the planar surface encompasses the channel port. A portion of the channel port surface region includes a conical recess which defines, at its bottom, the channel port. The outlet end of the conduit and the channel port surface regions are complementary in that they may be superimposed so as to co-locate the conduit outlet and the channel port. The leading edge of the weld projection is adapted for contact with the interior wall of the conical recess as the outlet end of the conduit is urged against the conical recess by a biasing force. The leading edge of the weld projection contacts the interior wall of the conical recess in a fashion that defines a circular line of contact. The weld projection, and the material in the interior wall of the conical recess that underlies the line of contact, are both formed of electrically resistive material suited to melting and subsequent fusion via resistive heating due to a brief application of an electric current. Accordingly, upon application of a current pulse that flows between the weld projection and the interior wall of the conical recess, the current density of the pulse is concentrated at the line of contact and is sufficient to cause resistive heating of the weld projection and the material that underlies the line of contact. The weld projection and the material that underlies the line of contact are melted, thereby becoming fused together. Upon cooling, the outlet end of the conduit and the interior wall of the conical recess are found to be fused, and the weld projection and the line of contact are merged and thus no longer distinguishable, thus joining the outlet end of the conduit and the channel port surface region such that a hermetic seal is imposed at the juncture of the superimposed conduit outlet and channel port.

Preferred embodiments of a fluid connector system constructed according to the present invention may be employed to attach a tubular fitting to a planar surface in a planar chromatographic assembly constructed for use in an analytical instrument. The planar chromatographic assembly includes a planar manifold, a heater assembly for establishing a temperature-controlled zone, an injector section, a separation column having inlet and outlet ends attached to selected internal fluid-bearing conduits in the pneumatic manifold and which is located within the temperature-controlled zone, and one or more fluid-handling functional devices attached to the pneumatic manifold. Channel ports are provided to offer fluid communication with respective etched channels in the planar manifold. One or more of the fluid-handling functional devices are connected to one or more ports on the planar manifold by way of a fluid connector system as described herein to thereby establish fluid communication with one or more respective channels.

The preferred embodiments of the fluid connector system are amenable to effect fluid coupling between a planar manifold and tubular device found on a variety of fluid-handling functional devices, including: a) passive devices such as a fluid coupler or a vent for coupling a fluid stream to or from a selected fluid-bearing conduit; b) active devices such as a valve, a fluid regulator, or a fluid flow input device (connectable to a fluid source) operable in response to a control signal from the control system for controlling fluid flow in one or more selected etched channels in the planar manifold, or c) signal generating devices such as a sensor or detector operable so as to provide sense or detection signal indicative of a characteristic of the fluid flow in an etched channel or in the separation column. Other preferred tubular devices include narrow bore metal tubing, metal capillary separation columns, and the like.

Fluid connections provided by the preferred embodiments are robust (i.e., the hermetic seal withstands operation in an adverse environment, e.g., an environment subject to rapid temperature changes or vibration), substantially free of dead volume, and offer excellent reliability and a long life. Such fluid connections allow an instrument such as a chromatograph to be provided in a compact assembly, thus enabling its use as a portable unit, or for easy attachment in a confined space with respect to a flow system to be analyzed, thus enabling an analysis of a chemical process in an "on-line", "at-line", or similarly oriented type of chemical process analysis.

Fluid connections that would previously be impossible or impractical to establish between a tubular device and a planar device may now be provided.

DETAILED DESCRIPTION OF THE PREFERRED EMBODIMENT

The present invention will find use in a variety of applications that benefit from effective connection of one or more fluid streams in respective fluid-bearing conduit to a planar device.

The apparatus and methods of the present invention are especially applicable to provide fluid connections between a port on a planar surface and a tubular device in a fluid system that effects the initiation, distribution, redirection, termination, control, sensing, and other types of fluid handling functions with respect to one or more of fluid streams (and such functions thus collectively defined herein as fluid handling functions); Liquids and gases are the preferred fluids according to the practice of the present invention, and the following description of the invention will describe the construction and operation of certain portions of an analytical instrument, and in particular of the fluid-tight connections of a gaseous stream in a gas chromatographic analytical system (hereinafter, a chromatograph). However, for the purposes of the following description, the term "fluid" will be considered to refer to all liquids, gases, mixtures of gases and liquids, supercritical fluids, and fluidized materials or mixtures, e.g., slurries, dispersions, etc.; in short, the term "fluid" refers to all types of fluids.

In the Figures and the description to follow, like nomenclature and numeric identifiers will refer to like components; signal lines are drawn schematically by single solid lines; fluid flow lines or channels are drawn schematically as double solid lines.

Figure 1:
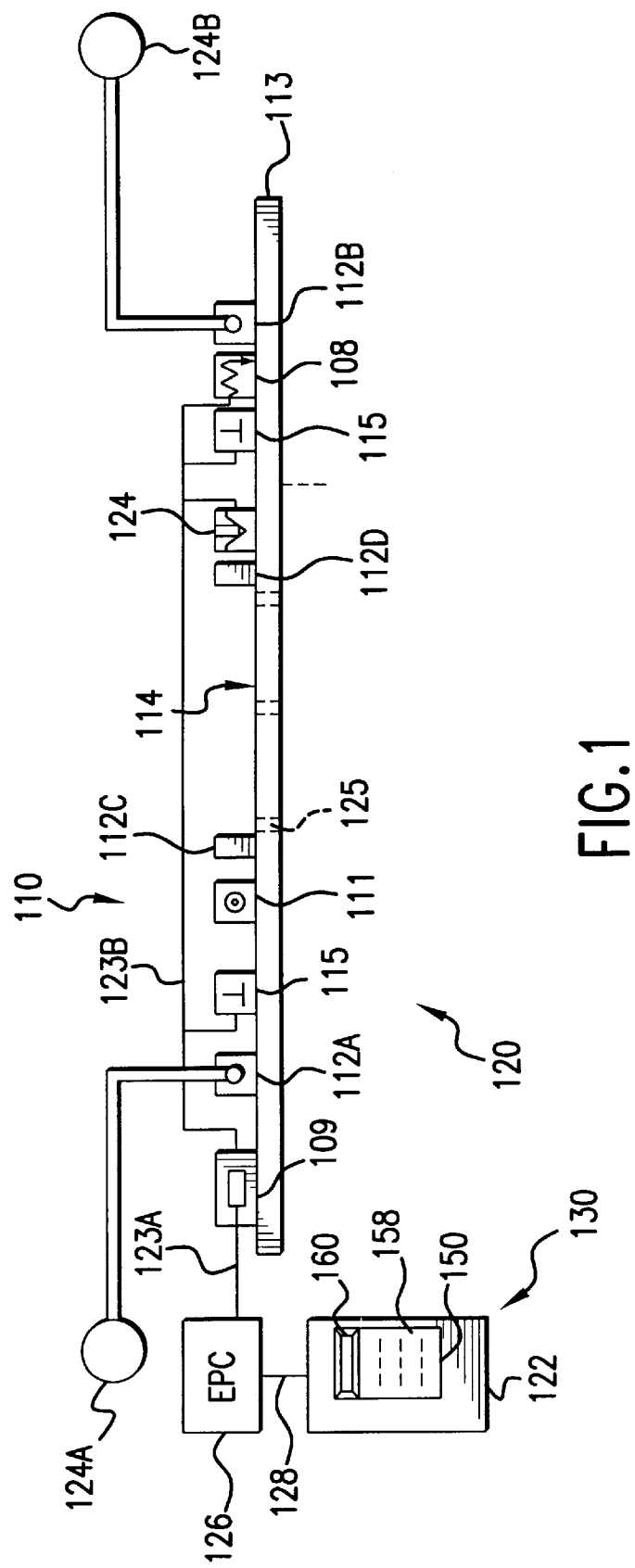
FIG. 1 is a simplified block diagram of an analytical instrument constructed to include a planar manifold assembly and a novel fluid connector system for use therein in accordance with the present invention.

An analytical instrument is shown in FIG. 1 and is generally designated as chromatograph 110 having a planar manifold assembly 120 and a control section 130. The planar manifold assembly 120 is provided in a compact configuration such that, in comparison to a conventional gas chromatograph, the planar manifold assembly 120 occupies less volume, has a smaller footprint, is amenable to configuration as a portable unit, is less complex and costly to manufacture, and consumes less operating power. In order to perform a chromatographic separation of a given sample compound, a sample is injected into the planar manifold assembly 120 with a pressurized carrier gas by means of a sample inlet 111. The carrier gas supplied to inlet 111 is provided from a source 124A through one or more fluid connectors 112A into a planar manifold 113, which incorporates internal channels capable of bearing fluid flow, each of which serve in part to control or redirect a plurality of gas flows. The detector gases are provided from respective sources (one such source 112B is shown) through respective fluid connectors 112B to the planar manifold 113. A separation column (not shown) may be attached to a portion of the planar manifold 113 at its inlet and outlet ends to selected channels 125 in the planar manifold 113 by respective fluid connectors 112C, 112D. The carrier gas/sample combination passing through column is exposed to a temperature profile by known means. During this profile of changing temperatures, the sample will separate into its components primarily due to differences in the interaction of each component with the column 114 at a given temperature. As the separated components exit the column, they are detected by a detector 124.

In a first feature of the present invention, at least some of the fluid-handling functional devices in the planar manifold assembly 120 are contemplated as being connected to the planar manifold 113 by way of preferred embodiments of a fluid connector system described herein. The contemplated fluid-handling functional devices include passive devices such as the aforementioned tubing, inlet 111, fluid connectors 112A, 112B, 112C, 112D; active devices such as valves 115, regulators (not shown in FIG. 1), and the like; and signal generating devices such as sensors 108, detector 124, and so on. The active devices and the signal generating devices are contemplated as being operated under control signals generated by the control section 130 on data and control lines 123A, 123B, and 128 connected to computer 122 and pneumatic controller 126. Accordingly, the computer 122, pneumatic controller 126, and planar manifold 113 may be operated to effect a variety of fluid handling functions. The planar manifold assembly 110 preferably includes one or more electronic signal connectors 109 and associated cabling (shown in simplified form as line 123B for clarity) for control, data, and power signals as may be needed. It is contemplated that for some applications an optional interface in the form of an electronic control panel 150 having a keypad 158 and a display 160 may be included.

Turning now to FIGS. 2–5, a preferred embodiment of a planar manifold 210 contemplated by the present invention includes a front plate 210A having front surface 210C and a back plate 210B having back surface 210D; these plates are sized and constructed to be superimposed and bonded together during the manufacturing process to form the planar manifold 210. Preferably, the front plate 210A and back plate 210B are machined from nickel-plated stainless steel and etched to provide an arrangement of etched channels 210E each capable of sustaining fluid flow. That is, the etched channels 210E form a predetermined array of internal channels when the front plate 210A and back plate 210B are bonded together to form the planar manifold 210.

In contrast to the conventional approach, wherein the task of forming complex interconnected flow paths usually involves the use of many discrete pieces of tubing and fittings through which the pieces of tubing can be attached, the planar manifold 210 replaces conventional manifolds at a fraction of the cost and with minimal labor. The planar manifold 210 is robust, rigid, shock proof, and unaffected by operation in a high temperature environment. Hence, the planar manifold 210 is intended as a primary structural support member of the embodiment 200, in addition to serving as a flow manifold for receiving fluid connections to fluid handling functional devices, and for managing a complex arrangement of fluid flows. Further details on the design and manufacturing of a planar manifold having etched channels therein may be found in commonly-assigned U.S. Pat. No. 5,567,868, issued to Craig et. al., the disclosure of which is included herein by reference.

As will now be described, certain ones of the etched channels such as channels 203A, 210E in one or both of the front and back plates 210A, 210B are connected, via one or more of the preferred embodiments of the present invention, to a selected fluid-handling functional device.

Figure 2A:
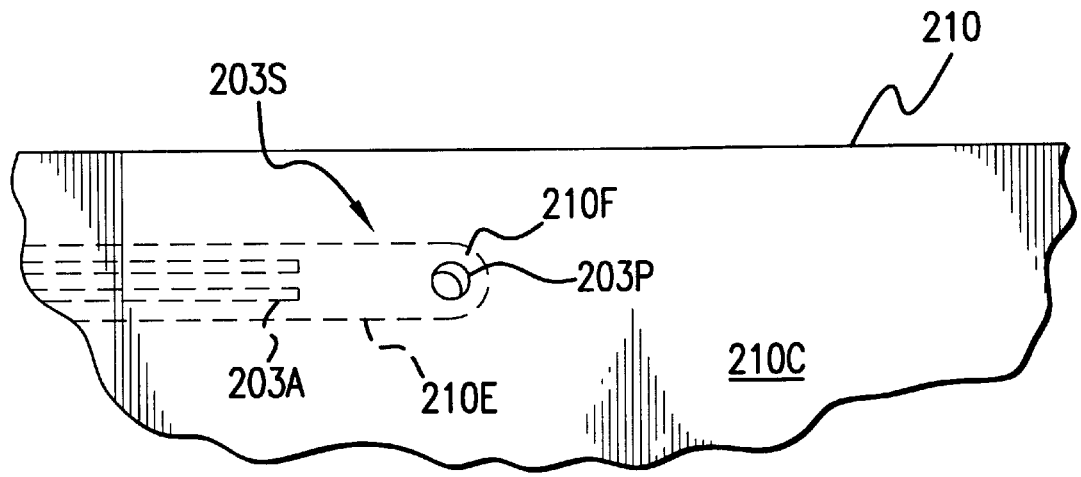
FIG. 2A is side perspective view of a portion of a planar surface included in the planar manifold assembly of FIG. 1, with certain components of the planar manifold assembly being omitted for clarity.
Figure 2B:
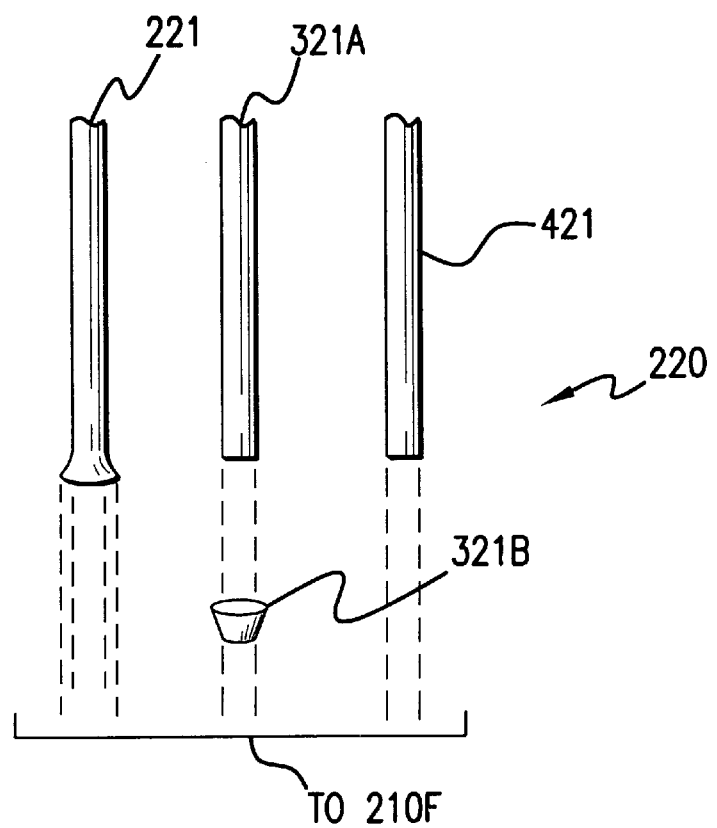
FIG. 2B is side perspective view of first, second, and third embodiments of a fluid connector system for connecting a tubular device to the planar manifold of FIG. 2A.

As illustrated in FIGS. 2A–2B, planar manifold 210 includes the front surface 210C having therein a variety of ports 203P and etched channels 210. Certain ones of the etched channels 210E may be directed to respective ones of the channel port surface regions 203S, each having a port 203P, being suitable for effecting fluid communication with a complementary conduit outlet in a selected one of three preferred embodiments of a fluid connector system 220. In particular, the etched channels 210E extend to the portion of the planar manifold 210 (preferably in the immediate vicinity of the port 203P) where an interface surface 210F is located.

Figure 3A:
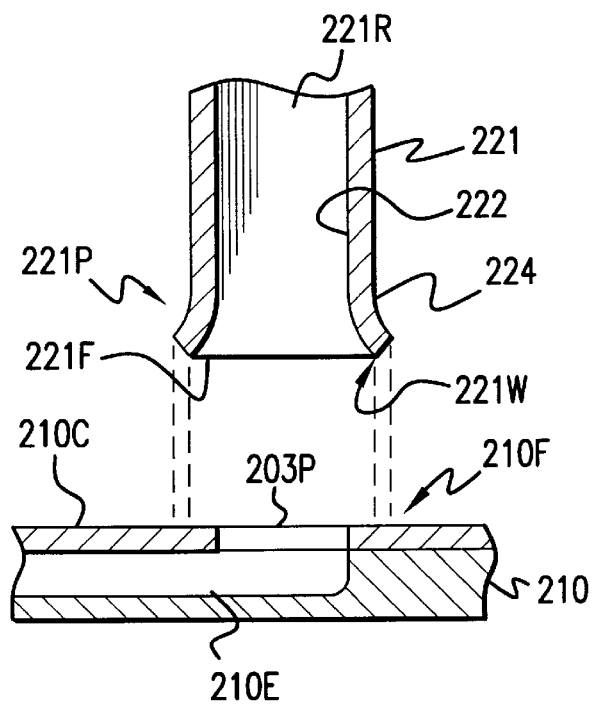
FIG. 3A is a cross-sectional exploded view of a portion of the first preferred embodiment of the fluid connector system shown in FIG. 2, prior to the step of projection welding.
Figure 3B:
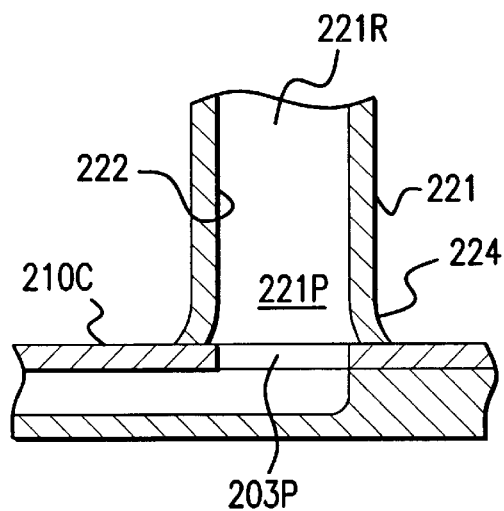
FIG. 3B illustrates the system after the completion of projection welding.

As illustrated in FIGS. 3A–3B, a first preferred embodiment of a fluid connector system includes a flared conduit 221 for establishing fluid communication between a channel 210E in the planar manifold 210 and a bore 221R in the conduit 221. The fluid connector system is designed to provide fluid communication between the internal bore 221R of the conduit 221 to the port 203P and hence to the etched channel 210E. The conduit 221 is constructed to include a flared outlet end 221P and generally cylindrical, parallel interior and exterior walls 222, 224. Impressing the conduit 221 onto the manifold 210 superimposes the leading edge of a flared interface surface 221F onto the interface surface 210F on the planar manifold 210. The bore 221R is thus superimposed over the port 203P. It is important to insure integrity and freedom from leakage in the fluid communication between the bore 221R and interface surfaces 222F and 210F. Accordingly, the flared outlet end 221P of the conduit 221 is sharply cut, thus allowing the leading-edge of the flared interface surface 221F to function as a circular weld projection 221W that encompasses the terminal end of the bore 222R. The conduit 221 is aligned coaxially with port 203P while being oriented perpendicularly to the interface surface 210F. By biasing the weld projection 221W against the interface surface 210F and upon application (by suitable electrode means not shown) of an electrical current pulse between the conduit 221 and the interface 210F, the line of contact between the weld projection 222W and the interface surface 210F is subject to a brief period of extremely high current density, whereupon the interface surface 221F is fused to the interface surface 210F. The conduit 221 is thereafter found to be rigidly fixed to the planar manifold 210 in an upright position, as illustrated in FIG. 4B, and the interface surfaces 210F, 221F are welded together. Accordingly, the bore 221R is unified in a fluid-tight connection with the etched channel 210E.

Figure 4A:
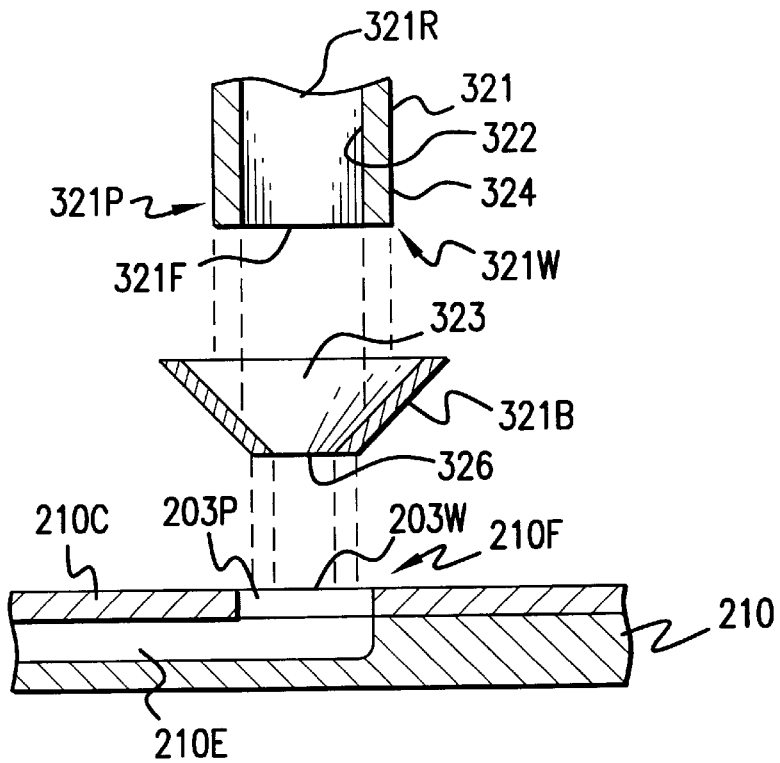
FIG. 4A is a cross-sectional exploded view of a portion of the second preferred embodiment of the fluid connector system shown in FIG. 2, prior to the step of projection welding.
Figure 4B:
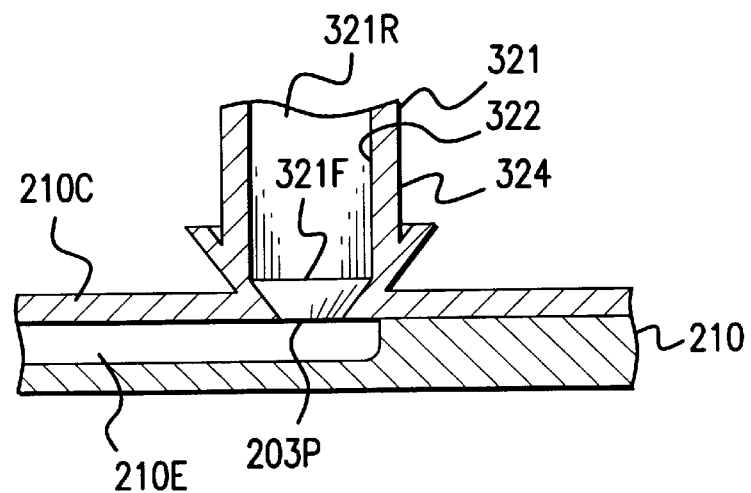
FIG. 4B illustrates the system after the completion of projection welding.

As illustrated in FIGS. 4A–4B, a second preferred embodiment of a fluid connector system includes a straight conduit 321 for establishing fluid communication between the channel 210E in the planar manifold 210 and a bore 321R in the conduit 321. Bore 321R is designed to provide fluid communication with the port 203P and hence to the etched channel 210E. The conduit 321 includes straight cylindrical parallel interior and exterior walls 322, 324. The conduit 321 is aligned coaxially with port 203P while being oriented perpendicularly to the surface 210C. The outlet end 321P of the conduit 321 is centered and impressed upon an interior surface 323 of a conical fitting 321B which in turn is centered and impressed upon an interface surface 210F in the manifold 210. The bore 421R is thus superimposed over a central opening 326 in the conical fitting 321B, so as allow it to communicate with the port 203P when superimposed. It is important to insure integrity and freedom from leakage in the fluid communication between the bore 321R and channel 210E at the junction of interface surface 321F with the interior surface 323, and at the junction of exterior surface 321B and the interface surface 210F. Accordingly, the outlet end 321P of the conduit 321 is sharply cut, thus allowing the interface surface 321F to include, at its peripheral edge, a weld projection 321W. The port 203P is also sharply cut in the surface 210C, thus affording, at its uppermost periphery, an inner edge that serves as a weld projection 203W. By biasing the weld projection 321W against the interior surface 323 and the exterior surface 321B against the weld projection 203W, and upon application (by suitable electrode means not shown) of an electrical current pulse between the conduit 421, conical fitting 321B, and the interface surface 210F, the two circular lines of contact between the weld projections 321W and 203W and the conical fitting 321B are subject to a brief period of extremely high current density, whereupon the interface surface 321F is fused to the interior surface 323 and the exterior surface 321B is fused to the interface surface 210F. The conduit 421 and conical fitting 321B are thereafter found to be rigidly fixed in the positions illustrated in FIG. 4B with respect to the planar manifold 210. Accordingly, the bore 321R is unified in fluid communication with the etched channel 210E.

Figure 5A:
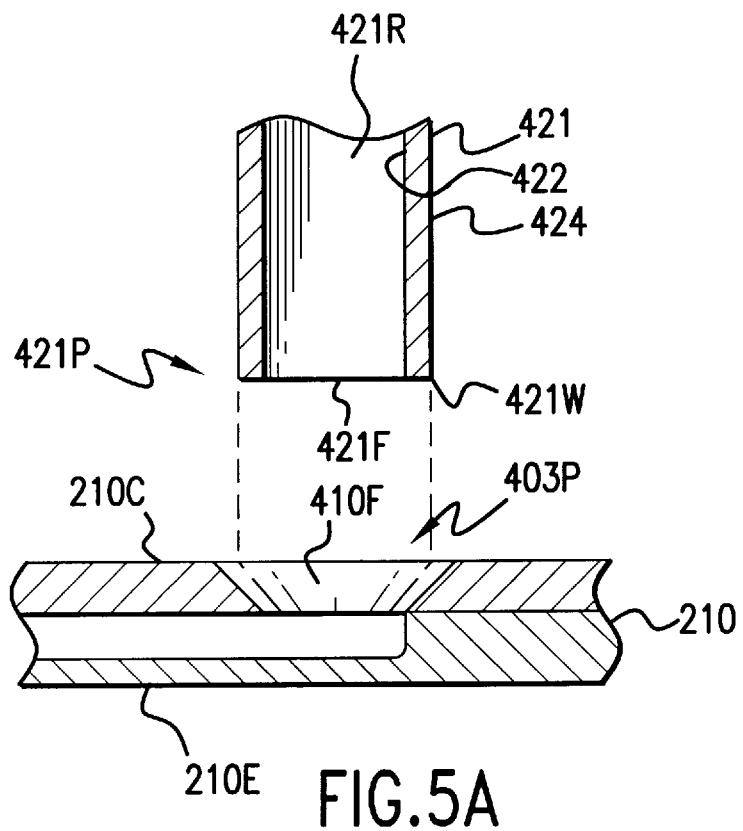
FIG. 5A is a cross-sectional exploded view of a portion of the third preferred embodiment of the fluid connector system shown in FIG. 2, prior to the step of projection welding.
Figure 5B:
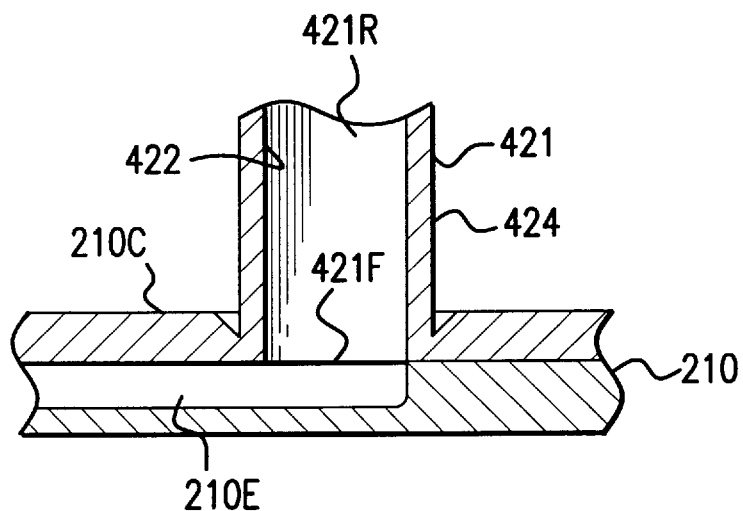
FIG. 5B illustrates the system after the completion of projection welding.

As illustrated in FIGS. 5A–5B, a third preferred embodiment of a fluid connector system includes a straight conduit 421 for establishing fluid communication between the channel 210E in the planar manifold 210 and a bore 421R in the conduit 421. Bore 421R is designed to provide fluid communication to the port 203P and hence to the etched channel 210E. The conduit 421 includes straight, cylindrical, parallel interior and exterior walls 422, 424. Impressing the conduit 421 onto the manifold 210 superimposes the leading edge of an interface surface 421F onto an interface surface 410F especially prepared to include a conical recess in the planar manifold 210. The bore 421R is thus superimposed over the port 203P. It is important to insure integrity and freedom from leakage in the fluid communication between the conduit 421 at the junction of interface surfaces 421F and 410F. Accordingly, the outlet end 421P of the conduit 221 is sharply cut, thus allowing the interface surface 221F to include, at its outermost peripheral edge, a weld projection 221W. The conduit 421 is aligned coaxially with port 203P while being oriented perpendicularly to the surface 210C. By biasing the weld projection 421W against the interface surface 410F and upon application (by suitable electrode means not shown) of an electrical current pulse between the conduit 421 and the interface surface 410F, the circular line of contact between the weld projection 421W and the interface surface 410F is subject to a brief period of extremely high current density, whereupon the interface surface 421F is fused to the interface surface 410F. The conduit 421 is thereafter found to be rigidly fixed in an upright position with respect to the planar manifold 210, and the interface surfaces 410F, 421F are welded together. Accordingly, the bore 421R is unified in fluid communication with the etched channel 210E.

Figure 6:
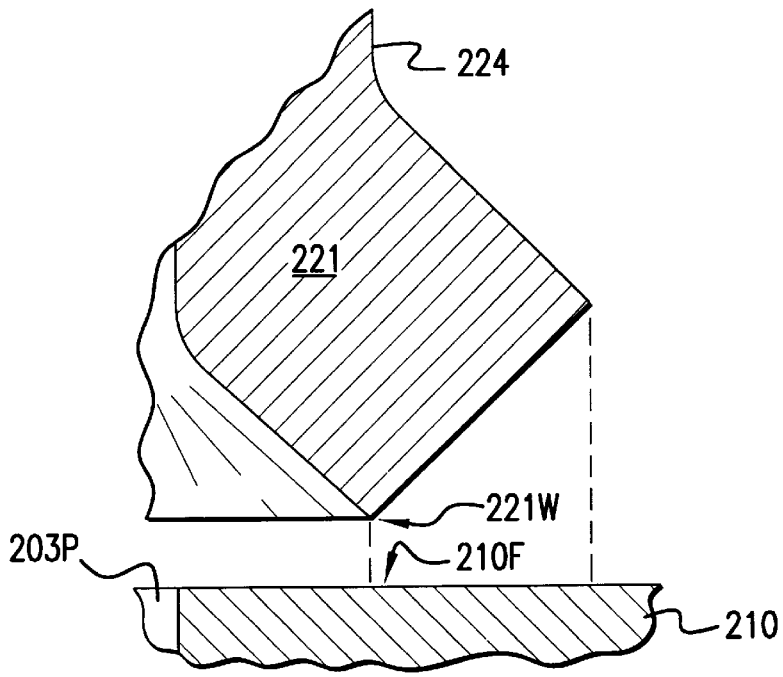
FIG. 6 is a cross-sectional view of the weld projection of the fluid connector of FIG. 3A just prior to contact with the planar manifold.
Figure 7:
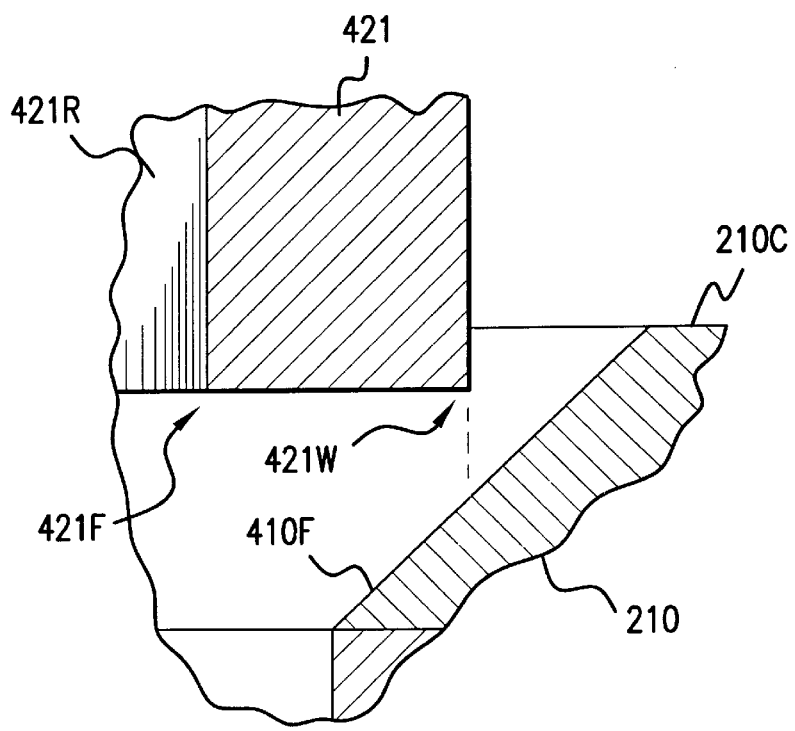
FIG. 7 is a cross-sectional view of the weld projection of the fluid connector of FIG. 5A just prior to contact with the planar manifold.

Preferred embodiments of the weld projections 221W, 321W, 421W, 203W are, as already described, each provided in the form of a sharply cut circular edge. For example, and as illustrated and FIGS. 6 and 7, the weld projection 221W is respectively formed by the interior peripheral edge of the outlet end of conduit 221; the weld projection 421W is respectively formed by the exterior peripheral edge of the outlet end of conduit 421.

The illustrated embodiments of a fluid connector system are useful in establishing a fluid connection between a tubular device and a planar surface on a fluid handling functional device, such as a valve, Inlet block, and the like, or between a tubular device and a planar surface on a planar device, such as a planar manifold assembly, and afford the following benefits and advantages. The overall system is compact and uses fewer conventional fluid connections, which would otherwise undesirably increase the overall volume of the system. Reliable fluid connections between fluid-handling functional devices (such as fittings, valves, sensors, and the like) may be provided in a plurality of flow paths in the illustrated planar manifold. More miniaturized fluid-handling functional devices may be connected to the planar surface.

A large number of fluid-handling functional paths may thus be integrated into a planar device having a compact, low-profile form factor in a fashion that heretofore would be difficult if not impossible to assemble using traditional tubular pipe, ferrules, and manual fittings. Also, considerable cost savings and improved reliability are realized by reduction of the number of connections necessary to achieve multiple flow paths. The fluid connections provided by the invention also reduce the complexity of an assembly that includes fluid connections to a planar surface on a planar device, which is desirable during the stages of manufacturing, assembly, repair, or modification of, e.g., an analytical instrument in which the planar device may be situated.

Another advantage is that a planar device may be constructed to include connections to certain conventional fluid-handling devices, such as a capillary separation column, that otherwise are difficult to connect to a planar surface, thus saving cost and providing for simpler manufacturing.

While the invention has been described and illustrated with reference to specific embodiments, those skilled in the art will recognize that modification and variations may be made without departing from the principles of the invention as described herein above and set forth in the following claims.

What is claimed is:

1. The method of joining a tubular member to a surface comprising:
   providing metal surface;
   supplying a metal tube having an annular end surface with a circular edge at its inside diameter thereof and with a circular edge at its outside diameter thereof;
   bringing one of the circular edges of the annular end surface into contact with the metal surface without bringing the other circular edge in to contact with the metal surface; and applying heat while the one circular edge is in contact with the metal surface and cooling to form a weld between the metal surface and the end of the metal tube.

2. The method of claim 1 wherein the circular edge is the outside diameter of the annular end surface is brought in contact with the inside curved surface which of a hollow truncated cone.

3. A product made according to the method of claim 1.

4. The method of joining a metal tube to a surface comprising:

providing a generally planar metal surface;

supplying a metal tube, the end of the tube having an annular end surface with a circular edge at its inside diameter thereof and with a circular edge at its outside diameter thereof, the end region of the tube being flared so that the tube ends at the circular edge at the inside diameter;

bringing the generally planar surface and the circular edge at the inside diameter of the annular end surface into contact; and applying heat while the circular edge is in contact with the generally planar surface to merge the metal of the end of the tube and forming a weld between the surface and the end of the tube.

5. The method of claim 4 wherein the tube is brought into perpendicular contact with the generally planar surface and the circular edge at the inside diameter of the annular end surface lies in a plane normal to the longitudinal axis of the tubular member.

6. The method of joining a tubular member to a surface comprising:

providing a generally planar surface of metal having an opening thereon;

supplying a metal tube, the end the tube having an annular end surface with a circular edge at its inside diameter thereof and with a circular edge at its outside diameter thereof, the end region of the tube being flared so that the member ends at the circular edge at the inside diameter;

bringing the circular edge at the inside diameter of the annular end surface into contact with the generally planar surface around the opening with the bore of the tubular member in communication with the opening ; and applying heat while the circular edge is in contact with the generally planar surface around the opening to merge the metal of the end of the tube and forming a weld between the surface and the end of the tube.

7. The method of claim 6 wherein the tube is brought into perpendicular contact with the generally planar surface around the opening and the circular edge at the inside diameter of the annular end surface lies in a plane normal to the longitudinal axis of the tube.

8. The method of joining a tube to a manifold of a chromatograph where the manifold has a channel therein that opens with a circular opening onto a planar surface of the manifold comprising:

supplying a metal tube, the end the tube having an annular end surface with a circular edge at its inside diameter thereof and with a circular edge at its outside diameter thereof, the end region of the tube being flared so that the member ends at the circular edge at the inside diameter;

bringing the circular edge at the inside diameter of the annular end surface into contact with the planar surface of the manifold around the circular opening with the bore of the tube in aligned co-axially with the opening; and applying heat while the circular edge is in contact with the generally planar surface around the opening to merge the metal of the end of the tube and forming a weld between the surface and the end of the tube.

9. A chromatograph made according to the method of claim 8.

10. The method of joining a tube to a surface comprising:

providing a metal wall having a generally planar exterior surface with an opening therethrough in the shape of a hollow truncated cone;

supplying a metal tube, the end the tube having an annular end surface with a circular edge at its inside diameter thereof and with a circular edge at its outside diameter thereof;

bringing the circular edge at the outside diameter of the annular end surface into contact with the curved wall surface the hollow truncated cone opening; and applying heat while the circular edge at the outside diameter of the annular surface is in contact with the converging wall surface of the opening to merge the metal of the end region of the tube and the metal wall to form a weld.

* * * * *